United States Patent [19]

McNamara et al.

[11] Patent Number: 4,704,383

[45] Date of Patent: Nov. 3, 1987

[54] NON-ANTIBACTERIAL TETRACYCLINE COMPOSITIONS POSSESSING ANTI-COLLAGENOLYTIC PROPERTIES AND METHODS OF PREPARING AND USING SAME

[75] Inventors: Thomas F. McNamara, Port Jefferson; Nungavaram S. Ramamurthy; Lorne M. Golub, both of Smithtown, all of N.Y.

[73] Assignee: The Research Foundation of State University of New York, Albany, N.Y.

[21] Appl. No.: 699,048

[22] Filed: Feb. 7, 1985

Related U.S. Application Data

[63] Continuation-in-part of Ser. No. 566,517, Dec. 29, 1983, Pat. No. 4,666,897.

[51] Int. Cl.$^4$ ............................................. A61K 31/65
[52] U.S. Cl. ................................................... 514/152
[58] Field of Search ......................................... 514/152

[56] References Cited

U.S. PATENT DOCUMENTS

| | | | |
|---|---|---|---|
| 2,895,880 | 7/1959 | Rosenthal | 514/152 |
| 3,304,227 | 2/1967 | Loveless | 514/152 |
| 3,636,202 | 1/1972 | Klein | 514/152 |
| 4,371,465 | 2/1983 | McGregor | 514/2 |
| 4,454,110 | 6/1984 | Cáslavsk et al. | 514/152 |

FOREIGN PATENT DOCUMENTS

| | | | |
|---|---|---|---|
| 787882 | 12/1957 | United Kingdom | 514/152 |
| 925282 | 5/1963 | United Kingdom | 514/152 |

OTHER PUBLICATIONS

Chemical Abstracts 100:96203a (1983).
Dreispach et al. Induchon of Collagenase Production in Vibrio B-30; J. Backeriol vol. 135, No. 2 (1978) pp. 521-527.

Primary Examiner—Albert T. Meyers
Assistant Examiner—John M. Kilcoyne
Attorney, Agent, or Firm—Cooper, Dunham, Griffin & Moran

[57] ABSTRACT

Tetracyclines having substantially no effective antibiotic or antibacterial activity and possessing anti-collagen-destructive enzyme activity or anti-collagenase activity and compositions containing the same have been found useful as anti-collagenolytic agents. Such tetracyclines and compositions containing the same are useful in the treatment of periodontal diseases, corneal ulcers, bone deficiency disorders, rheumatoid arthritis diseases characterized by excessive collagen destruction. A special aspect of this invention involves the incorporation of such tetracyclines in animal feed compositions for improved animal nutrition, such as may be evidenced by increased weight gain.

5 Claims, 6 Drawing Figures

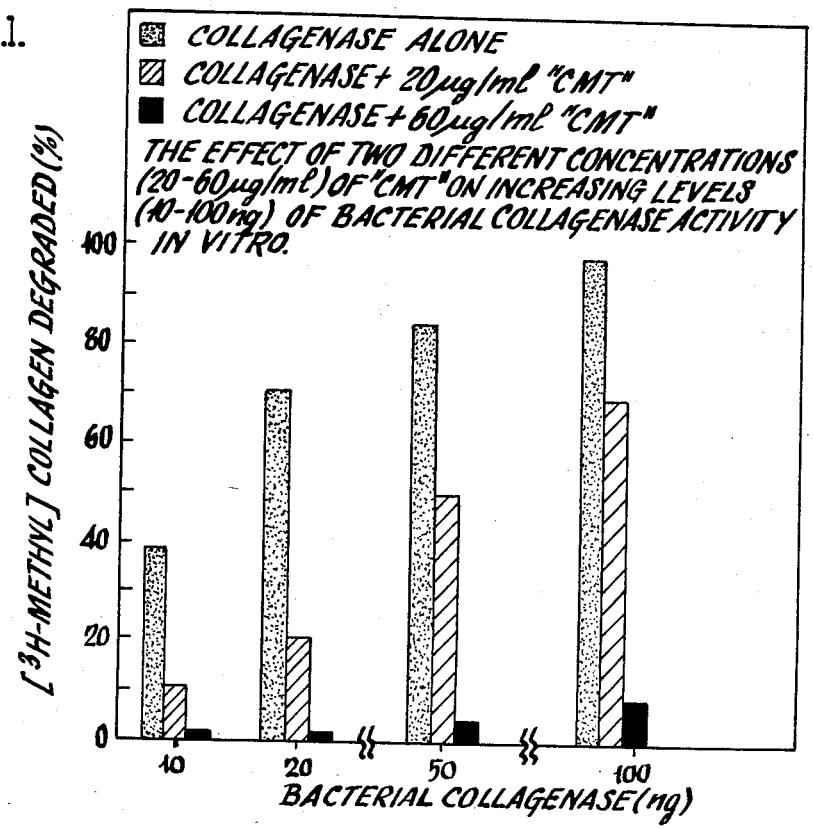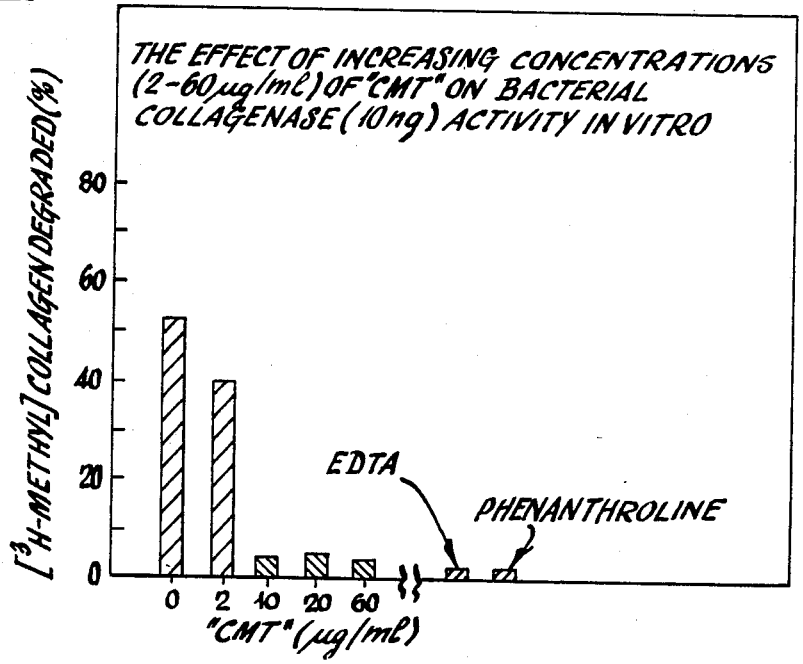

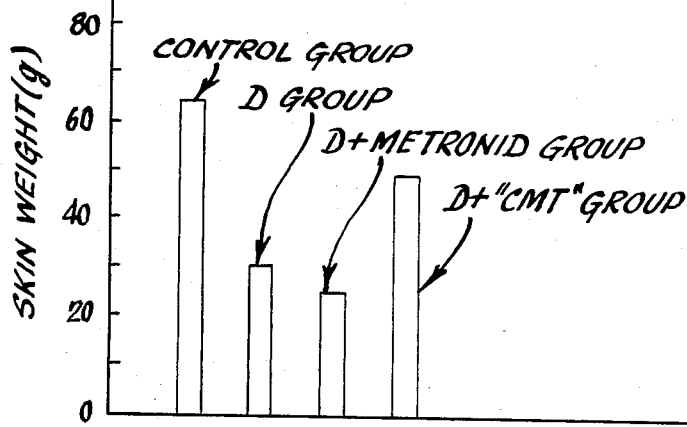
Fig. 5. THE ORAL ADMINISTRATION OF METRONIDAZOLE OR "CMT" (20 mg per day) TO DIABETIC RATS: EFFECT ON SKIN WEIGHT 37 DAYS AFTER INDUCING DIABETES AND INITIATING DRUG THERAPY.
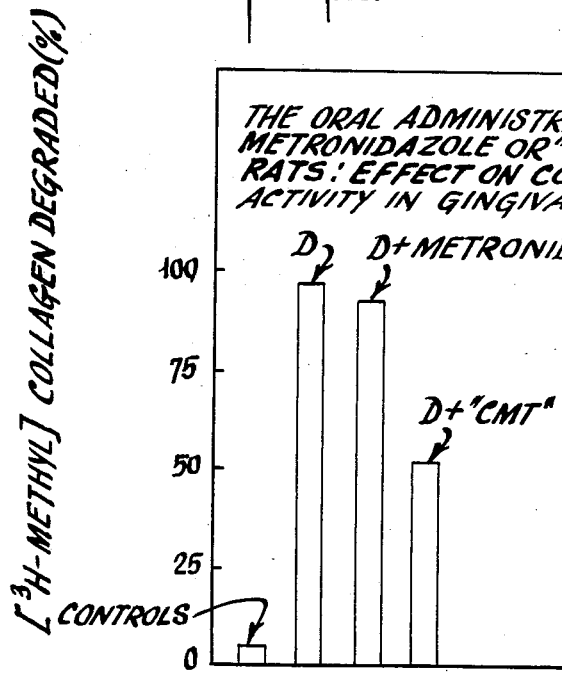
Fig. 6. THE ORAL ADMINISTRATION OF METRONIDAZOLE OR "CMT" TO DIABETIC RATS: EFFECT ON COLLAGENASE ACTIVITY IN GINGIVAL TISSUE.

NON-ANTIBACTERIAL TETRACYCLINE COMPOSITIONS POSSESSING ANTI-COLLAGENOLYTIC PROPERTIES AND METHODS OF PREPARING AND USING SAME

This application is a continuation-in-part of application Ser. No. 566,517 filed Dec. 29, 1983, now U.S. Pat. No. 4,666,897. The disclosures of the above-identified application are herein incorporated and made part of this disclosure.

BACKGROUND OF THE INVENTION

Tetracyclines are well known broad spectrum antibiotics. Recently antibiotic tetracyclines have also been discovered to inhibit the activity of collagen destructive enzymes, e.g. mammalian collagenase, macrophage elastase and bacterial collagenases. For example, tetracyclines have recently been found to be useful in the treatment of periodontal diseases, severe progressive adult periodontitis and localized juvenile periodontitis. Antibiotic tetracyclines are also useful in the treatment of non-infected corneal ulcers, in the treatment of pathologically excessive bone resorption, in the treatment of joint destruction involved with rheumatoid arthritis and generally in the treatment of those diseases characterized by excessive collagen destruction.

In vitro tests have shown that antibiotic tetracyclines (1) inhibit leukocyte and chondrocyte collagenase activity;

(2) reduce bone resorption in organ culture induced by either parathyroid hormone, bacterial endotoxin or prostaglandin $E_2$; and (3) reduce macrophage collagenase and elastase activity in cell culture.

Also, in in vivo tests the antibiotic tetracycline, minocycline, in the treatment of diabetic rat was found to (a) reduce pathologically excessive collagenase activity in gingiva and skin;

(b) reduce pathological skin collagen resorption, and (3) reduce pathologically excessive alveolar bone loss.

Moreover, clinically, the antibiotic tetracyclines (Minocin, Achromycin and Vibramycin) at regular and low-dose levels were found to reduce collagenase activity in human periodontal pockets and regular dose levels of tetracycline brought about the healing of refractory non-infected corneal ulcers in humans, lesions which are believed to be mediated by mammalian collagenase.

However, although the commercially available antibiotic tetracyclines are effective as anti-collagenolytic agents, long term use, either continuously or episodically, e.g. two weeks on-three months off-two weeks on-three months off, is subject to the usual complications of long term antibiotic usage, such as intestinal disburbance, overgrowth of yeast and fungi, the development of antibiotic resistant bacteria, etc.

Accordingly, it is an object of this invention to provide compositions and therapies based on tetracyclines, and particularly the utilization of tetracyclines which have anti-collagenolytic activity in the treatment of diseases or conditions characterized by excessive collagon destruction, without at the same time giving rise to the usual complications involved with long term antibiotic use.

It is another object of this invention to provide tetracycline-containing compositions and the use of such commpositions as anti-collagenase agents while at the same time providing novel compositions and applications of such compositions in the treatment of various diseases and conditions characterized by excessive collagen destruction.

It is a special object or aspect of this invention to provide tetracycline compositions having improved properties, such as animal feed compositions containing tetracyclines which are effective when supplied or administered to animals not only as anti-collagenolytic agents but which also provide improved animal nutrition.

Current usage of the antibiotic tetracycline as an additive to animal feed for promoting improved feed conversion and weight gain has been found to have the adverse effect of producing the overgrowth of resistant organisms which are presently considered to be hazardous to human health. By the practice of this invention this adverse effect is eliminated while at the same time animal weight gain is promoted.

How these and other objects of this invention are achieved will become apparent in the light of the accompanying disclosure and drawings wherein:

FIG. 1 graphically illustrates the effectiveness of a tetracycline of this invention in reducing bacterial collagenase activity in vitro;

FIG. 2 graphically illustrates the effect of increasing concentrations of a tetracycline of this invention with respect to bacterial collagenase activity in vitro;

FIG. 3 graphically illustrates the effect of increasing concentrations of a tetracycline of this invention on rat polymorphonuclear leukocyte collagenase activity in vitro;

FIG. 4 graphically illustrates body weight gain of diabetic rats subjected to oral administration of a tetracycline of this invention compared to other rats to which other agents have been administered;

FIG. 5 graphically illustrates the effect on skin weight of diabetic rats administered with a tetracycline of this invention; and FIG. 6 graphically illustrates the effect in rats on collagenase activity in gingival tissue after the administration of a tetracycline of this invention.

SUMMARY OF THE INVENTION

It has been discovered that tetracyclines which have substantially no effective antibiotic or antibacterial activity possess anti-collagen-destructive enzyme activity or anti-collagenase activity. More particularly, it has been discovered that tetracyclines which have substantially no effective antibiotic or antibacterial activity possess the ability to inhibit collagenolytic enzyme activity and collagen resorption.

Tetracyclines are characterized by four carbocyclic rings and are well known antimicrobials or antibiotics. Not all tetracyclines, however, possess antimicrobial or antibiotic properties. A number of tetracyclines exhibit substantially no antimicrobial or antibacterial activity whereas other tetracyclines, although exhibiting some antimicrobial or antibiotic activity, do not posses such antimicrobial or antibacterial activity to the extent that they are useful as chemotherapeutic agents or as antibiotics in the treatment of diseases. Those tetracyclines which exhibit no or substantially no or insufficient antimicrobial or antibiotic activity are usefully employed in the practices of this invention. Especially useful in the practices of this invention is the tetracycline, dedimethylaminotetracycline. As indicated, however, other tetracyclines which do not possess sufficient, if any, antimicrobial activity are also useful in the practices of this invention.

Generally, tetracyclines, as has now been discovered, whether possessing antimicrobial or antibiotic activity or not, all posses anti-collagen-destructive enzyme activity or anti-collagenase activity. This anti-collagenase activity appears to be attributable to the unique structure of tetracyclines, i.e. the special four carbocyclic ring structure which is characteristic of and possessed by the tetracyclines.

As an observation, it is believed that the carbonyl moieties in the carbocyclic ring nucleus of the tetracycline are important to the anti-collagenolytic activity of these compounds because they chelate the metal ions calcium and zinc. This is an important property since the collagenolytic enzymes mentioned are metal dependent.

The action of the tetracyclines, when employed in the treatment of humans or animals suffering from a condition or disease characterized by excessive collagen destruction in accordance with the practices of this invention as anti-collagenolytic agents, appears to be systemic, although the tetracyclines may be employed topically, such as direct application to the gingival tissue, such as in the case of the treatment of periodonitis wherein excessive collagenase activity is involved and skin as in the treatment of ulcerative lesions, such as decubitus ulcers, diabetic ulcers, epidermolysis bullosa. In the practices of this invention the tetracyclines may be employed in any of the known modes of application appropriate for the treatment of the condition involved. The dosage of the non-antimicrobial or non-antibiotic tetracyclines of this invention is an effective anti-collagenase amount to reduce collagenase activity or when employed as an anti-collagenolytic agent could be the same as or slightly greater than the dosage of conventional tetracyclines when used as antimicrobial or antibiotic agents. In addition, however, the dosage can be substantially below or but a fraction or minor amount of such standard dosages or levels at which conventional antimicrobial tetracyclines are employed, such as about 5–50% of the standard therapeutic dosages with respect to the utilization of antimicrobial or antibiotic tetracyclines when employed in the treatment of diseases.

One commercially important aspect of the practices of this invention involves the utilization of the special non-antimicrobial or non-antibiotic tetracyclines, such as dedimethylaminotetracycline as an additive to animal feeds. Animal feed for ruminant, non-ruminant and ruminant-related animals usually comprises a mixture of grains, proteins, amino acids, minerals, vitamins and additives, such as preservatives, (antioxidants, bacteriostats, fungistats) and supplements that help protect the animal against parasites and diseases. The advantage of the use of the special tetracyclines in accordance with this invention as a component or additive in animal feed is that such a use would likely not give rise to antibiotic resistant strains of bacteria. The primary purpose of incorporating the special type tetracyclines of this invention in animal feed is as an anti-collagenolytic agent to improve animal nutrition and body weight and the tetracyclines of this invention are incorporated in or present in the animal fat in an effective anti-collagenase amount and/or for enhancing feed conversion and growth promotion.

By way of example as to the concentration or amount of the special tetracyclines of this invention incorporated in animal feeds, for poultry feeds for chickens, turkeys and broilers, the amount of the tetracycline incorporated in the feed would be in the range from about 10 grams to about 200 grams per ton of feed. With respect to feed for beef cattle for young calfs up to about 12 weeks of age, the amount of the tetracycline in the feed should be such that about 0.1 mg to about 1.0 mg per pound of calf weight per day is taken up by the calf upon consumption of the feed. With respect to beef cattle, the amount of tetracycline present in the feed should be such that the animal takes up or consumes from about 75 mg to about 300 mg per pound per day from the tetracycline-containing feed.

DETAILED DESCRIPTION OF THE INVENTION

Figure 3:
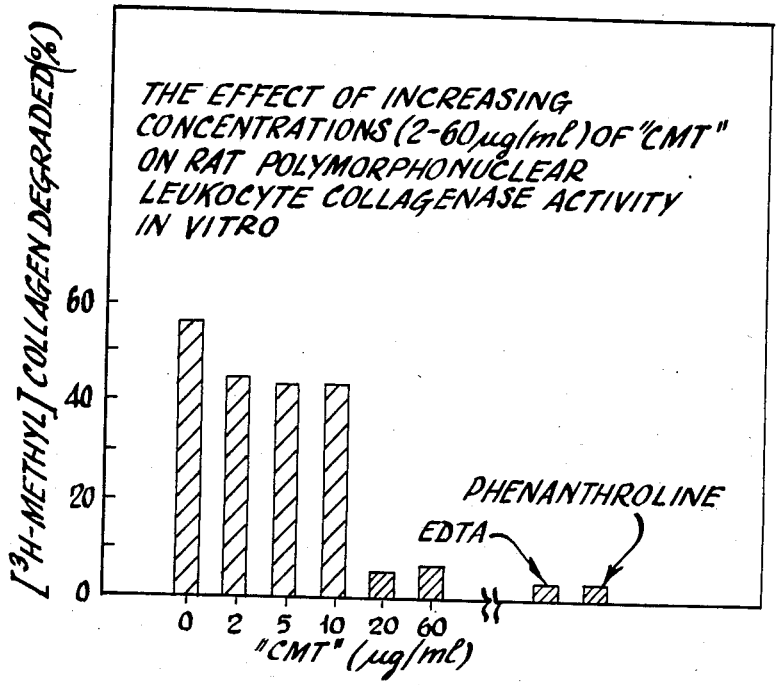

Preparation of Stock Solutions of Tetracycline, Minocycline and Dedimethylaminotetracycline (CMT)

Stock solutions of minocycline, dedimethylaminotetracycline (CMT) and tetracycline were prepared as aqueous solutions. These solutions were to be used to determine the antibacterial activity of each of these tetracyclines. The minocycline was obtained from Sigma Chemical Company, St. Louis, Mo. Lot #60F-0048. The tetracycline was also obtained from Sigma Chemical Company, St. Louis, Mo. Lot #103F0350 and the dedimethylaminotetracycline was synthetically prepared in accordance within the method of J. H. Boothe et al, J. Am. Chem. Soc., Vol. 80, page 1654 (1958) and J. R. D. McCormick et al., J. Am. Chem. Soc., Vol. 79, page 2849 (1957). The stock solutions were prepared as aqueous solutions containing 100 micrograms per milliliter of each of the compounds. To 10.00 mg. of either minocycline, tetracycline or dedimethylaminotetracycline 10 ml of distilled water was added and the suspension was swirled in a 100.0 ml volumetric flask. To each 10 ml suspension of the compound 1.0 ml of 1.0 N sodium hydroxide was added to produce a clear solution of each compound. Approximately 70 ml of distilled water was added to each solution and the pH was adjusted to a pH of 8.0 to 8.3 by the addition of the appropriate amount of 1.0 N hydrochloric acid. Each solution was then made up to 100.00 ml in the volumetric flask by the addition of distilled water. The final concentration of each of these compounds was 100 micrograms per ml. The stock solutions were stored in the refrigerator until they were used. Stock solutions were made fresh daily.

EVIDENCE OF LOSS OF ANTIMICROBIAL ACTIVITY

In vitro evidence:

In order to demonstrate that the dedimethylaminotetracyclcine (CMT) had reduced antimicrobial activity a comparison was made of the minimum inhibitory concentration (MIC) of each of the compounds. A comparison of the MIC of minocycline, tetracycline and dedimethylaminotetracycline were carried out in the following manner. To a series of tubes containing 3.0 ml of sterile Brain Heart Infusion (BHT) broth (DIFCO) appropriate amounts of the stock solutions of minocycline, dedimethylaminotetracycline and tetracycline were added to produce concentrations as shown in Table 1. Each tube was then adjusted with sterile BHI broth to a final volume of 4.0 ml. Each tube in the series was then inoculated with 0.1 ml of a 24 hour broth culture of Bacillus cereus which had been incubated at 37° C. The tubes were then vortexed and incubated at 37° C. for 24 hours. The tubes were then read for the presence or absence of growth which was determined by turbidity. The results of these comparative evaluations for antimicrobial activity are recorded in Table 1. It was evident that the dedimethyl-aminotetracycline has no detectable antibacterial activity against *Bacillus cereus.* It was more than 100 fold less active than tetracycline and more than 1,000 fold less active than minocycline. *Bacillus cereus* was used as the test organism because it is routinely used for tetracycline assays due to its extreme sensitivity to these antibiotics. The organism was obtained from the American Type Culture Collection (ATCC #11778).

TABLE I

Summary of the results of the in vitro evaluation of the antibacterial activity of minocycline, tetracycline and dedimethylaminotetracycline

| Antibiotic Conc. (μg/ml) | Minocycline | Antibiotic tetracycline | dedimethylamino-tetracycline |
|---|---|---|---|
| 2.5 | − | − | + |
| 2.0 | − | − | + |
| 1.5 | − | − | + |
| 1.0 | − | − | + |
| 0.5 | − | − | + |
| 0.1 | − | − | + |
| 0.025 | − | − | + |
| 0.010 | − | + | + |
| 0.005 | − | + | + |
| 0.0025 | − | + | + |
| 0.001 | + | + | + |

1 - *Bacillus cereus* was selected for this evaluation due to its sensitivity to tetracycline and its use for tetracycline antibiotic assays.
2 - + = growth
   − = no growth In vivo evidence:

Conventional animals and animals rendered diabetic were either not treated or treated with metronidazol or dedimethylaminotetracycline in a comparative study to determine the in vivo activity of dedimethylaminotetracycline.

In this study four different groups of rats were utilized. Group I was an untreated control group of conventional rats harboring a normal oral flora; Group II was an untreated control group of diabetic rats rendered diabetic by administration of streptozocin; Group III was a diabetic group treated orally with metronidazol and Group IV was a diabetic group of animals treated orally with dedimethylaminotetracycline.

At the conclusion of the experiment the rats were sacrificed and samples were removed with sterile currettes from the gingival margin of the molar teeth of rats from each of these groups of animals and transferred to broth and incubated for 72 hours at 37° C. The organisms isolated were compared to determine if there was any major change in the composition of the flora following the administration of either metronidazol or dedimethylaminotetracycline.

The results of the isolation and identification of the organisms obtained from gingival samples indicated that: (1) the untreated conventional control animals had slightly more organisms present than the animals in any of the other groups and were easily identified by the amount of growth and by the bacterial compositions, (2) the diabetic animals receiving metronidazol produced less growth from the gingival samples than any other group and had predominantly Gram positive cocci; (3) the untreated diabetic control animals and the diabetic animals receiving dedimethylaminotetracycline were essentially indistinguishable in the amount of growth obtained from the gingival samples and in the bacterial composition of each sample. These results are summarized in Table 2.

These in vivo studies clearly demonstrated that metronidazol preferentially suppressed the Gram negative anaerobic organisms in the crevicular microflora, as expected, whereas the dedimethylaminotetracycline or CMT did not have any detectable effect on the crevicular microflora in contrast to the effect of antibiotic tetracyclines.

Golub et al., *J. Periodontal Res.* 18: 516, 1983 demonstrated that an antibiotic tetracycline suppressed the gram-neg anaerobic organisms in the crevicular flora of the diabetic rat, similar to the effect described above for metronidazole.

TABLE 2

Summary of the results of the organisms isolated from untreated animals (conventional/diabetic) and animals treated with either metronidazol or minocycline (diabetic)

| | Conventional | Diabetic | | |
|---|---|---|---|---|
| Organisms | Untreated | Untreated | Metronidazol | CMT* |
| *E. coli* | + | + | + | + |
| Bacteroides | + | − | − | − |
| Fusobacterium | + | + | − | + |
| Proteus | + | − | − | − |
| Veillonella | + | + | − | + |
| Leptotrichia | + | − | − | − |
| Stretpococcus | | | | |
| alpha hemolytic | − | − | + | − |
| beta hemolytic | − | − | + | − |
| gamma hemolytic | + | + | + | + |
| Actinomyces | + | + | + | + |
| Lactobacillus | + | − | − | + |
| Staphylacoccus | − | + | + | + |
| Bifidobacterium | + | − | − | − |
| Candida | − | (±) | − | − |

*chemically modified tetracycline
+ = present
− = not present

EVIDENCE OF ANTI-COLLAGENOLYTIC ENZYME ACTIVITY

In Vitro Evidence:

Bacterial collagenase (from C. histolyticum), which like mammalian collagenase is a calcium dependent metallo-protease, was incubated for 18 hrs. at 27° C. with [$^3$H-methyl] collagen in the presence of 0, 20 or 60 ug/ml of CMT and the results are shown in FIG. 1. In the absence of CMT, increasing the bacterial collagenase levels in the incubation mixture from 10–100 ng) increased the degradation of the radiolabeled collagen substrate (from 40–90%), as expected. A similar pattern was seen when 20 ug/ml CMT was added, however, at all levels of bacterial collagenase (10–100 ng) the breakdown of collagen was lower than that seen in the absence of CMT. Increasing the concentration of CMT to 60 ug/ml essentially completely inhibited collagenase activity at all of the enzyme levels tested.

Another experiment was carried out. In this experiment, a single level of bacterial collagenase was incubated (a) with a wide range of concentrations of CMT (0, 2, 10, 20 and 60 ug/ml) and (b) with the known inhibitors of metallo-proteases, EDTA and phenanthroline. As in the first experiment, 10 ng of collagenase degraded about half of the available radiolabeled collagen substrate after an 18 hr. incubation at 27° C. in the absence of CMT, FIG. 2. The very low concentration of 2 ug/ml CMT inhibited collagenase activity by about 20% while the concentrations of 10–60 ug/ml CMT reduced activity about 90%. These higher concentrations of CMT inhibited collagenase activity by the same extent as the chelating agents, EDTA and phenanthroline, consistent with the hypothesis that the metal binding characteristics of the tetracyclines (including CMT) are responsible, at least in part, for their anti-collagenolytic enzyme properties.

A third experiment was carried out and the results are presented in FIG. 3. In this experiment radiolabeled collagen molecules were incubated (18 hrs., 27° C.) with an extract of rat leukocytes known to contain collagenolytic enzyme activity. This mammalian collagenass preparation was incubated with 0-60 ug/ml CMT or with the collagenase - inhibitors, EDTA or phenanthroline. The collagenase by itself degraded about 55% of available collagen substrate. In this experiment, 2-10 ug/ml CMT reduced the collagenase activity by about 20% while 20 and 60 ug/ml reduced the activity about 85%. EDTA and phenanthroline, two metal chelating agents, completely inhibited the activity of this mammalian collagenase, as expected, since leukocyte collagenase is known to depend on the presence of the metal ions, calcium and zinc, for normal activity. It is believed that the reason why this mammalian collagenase preparation required a higher concentration of CMT, than the bacterial collagenase preparation, to achieve the same degree of inhibition was two-fold: Firstly, the mammalian collagenase was a relatively impure enzyme compared to the highly purified bacterial enzyme. Thus, the CMT could have reacted with other metalloproteases (e.g. gelatinase) in the leukocyte preparation, in addition to reacting with collagenase, thus effectively reducing the inhibitor CMT/collagenase ratio. Secondly, leukocytes contain a high level of calcium ions and earlier experiments demonstrated that adding calcium to a collagenase/tetracyline mixture could overcome the inhibition of the enzyme activity.

In vivo evidence: Four separate groups of rats were set up, one group (controls) was left untreated throughout the entire protocol, the second (the diabetic or D group) was made diabetic by I.V. injection of Streptozotocin as described previously, the third group was made diabetic and then administered by the oral route 75 mg per day of the antibiotic, metronidazole (D+metronid. group), and the fourth group was made diabetic and orally administered on a daily basis 20 mg per day "CMT" (D+"CMT" group). These doses are 1/10 of the daily doses of each of these drugs when administered for therapeutic reasons to humans. The 1/10 value is the same dose that was administered to diabetic rats in previous studies using minocycline and which was found to produce beneficial changes in rats' connective tissues. At several time periods during the experimental protocol, the rats were weighed. On the final day of the experiment (day 37), a blood sample was taken from each rat for glucose analysis, the animals were weighed and then killed. The entire skin from each rat (except for that over the head, paws, genitals) and the buccal gingiva were dissected, weighed, minced, extracted (all procedures at 4° C.) and the extracts partially purified by ammonium sulfate precipitation. The collagenase activity in the skin and gingival extracts was measured after incubation with radiolabeled collagen as the substrate. (Skin extract was incubated at 35° C., 48 hrs., with $^{14}C$ glycine labeled collagen fibrils, while gingival extract was incubated at 27° C., 18 hrs., with [$^3H$-methyl] collagen molecules).

Just prior to killing the rats, a subginival plaque sample was taken from each animal from the maxillary areas. The samples were immediately placed into preduced broth (to protect the anaerobic microorganisms), incubated under anaerobic conditions, and the relative numbers of the Gram-positive, Gram-negative and motile microorganisms were assessed.

Figure 4:
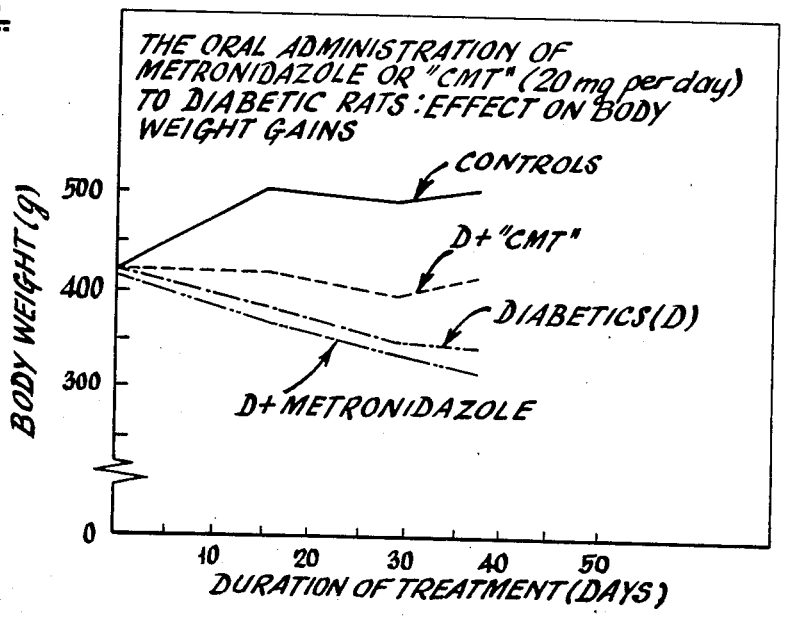

As shown in FIG. 4, the control rats, over the 37 day protocol, gained weight while the untreated diabetics (D group) progressively lost weight. Daily metronidazole therapy therapy had no effect in retarding the weight loss in the D rats, whereas daily treatment of the D rats with CMT completely inhibited body weight loss. In addition, towards the end of the experiment after [day 30] the "D" rats treated with CMT began to gain weight in a manner paralleling the non-diabetic controls while the untreated "D" rats during the same time period continued to lose weight.

The data in FIG. 5 shows a similar pattern of change. The D and D+metronid groups lost more than 50% of the skin mass by the end of the 37-day protocol, whereas treating the D rats with CMT on a daily basis inhibited the loss of skin mass (skin loss is a complication of the diabetic condition).

The data in Table 3 shows that all of the diabetic groups (D group; D+metronid groups; D+CMT group) were severely hyperglycemic (638-850 mg % blood glucose levels) compared to the normoglycemic (104 mg %) control rats. Treating the diabetic rats with metronidazole had absolutely no effect on the pathologically excessive collagenase activity in the diabetics' skins, Table 3, or in the diabetics gingiva, FIG. 6, even though the blood glucose in the metronidazole (antimicrobial)-treated rats was slightly reduced Table 3. In marked contrast, even though the CMT treatment appeared to have a lesser effect than metronidazole on blood glucose concentration, this modified tetracycline dramatically inhibited skin and gingival collagenase activity by about 50%, Table 3 and FIG. 6. These data demonstrate that CMT inhibits mammalian collagenase activity (and collagen resorption) in vivo, like standard antibiotic tetracyclines, but can accomplish this therapeutic effect without significantly affecting the crevicular microflora.

TABLE 3

Diabetes Stimulates the Collagenase Activity in Rat Skin: Effect of Orally Administered Metronidazole and "CMT"

| Experimental Group of rats | No. of rats per group | Blood glucose concentration (mg %)* | Collagenase Activity in skin extracts: | |
|---|---|---|---|---|
| | | | % $^{14}C$—collagen degraded* | % reduction in D group due to drug therapy |
| Controls | 4 | 103 ± 8 | 5.2 ± 0.9 | — |
| Diabetics (D) | 3 | 850 ± 35 | 47.3 ± 0.3 | — |
| D + Metronid. | 5 | 638 ± 22 | 46.0 ± 3.0 | 2.7 |

TABLE 3-continued

Diabetes Stimulates the Collagenase Activity in Rat Skin: Effect of Orally Administered Metronidazole and "CMT"

| Experimental Group of rats | No. of rats per group | Blood glucose concentration (mg %)* | Collagenase Activity in skin extracts: | |
|---|---|---|---|---|
| | | | % $^{14}$C—collagen degraded* | % reduction in D group due to drug therapy |
| D + "CMT" | 4 | 713 ± 31 | 20.9 ± 3.2 | 55.8 |

*Each value represents the mean ± S.E.M.

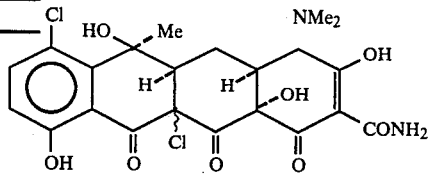

Although emphasis in this disclosure and the practices of this invention has been placed on the dedimethylaminotetracycline as the non-antimicrobial or non-antibacterial tetracycline, other substantially nonantimicrobial or non-antibacterial tetracyclines are also useful, such as 6α-benzylthiomethylene tetracycline having the structural formula:

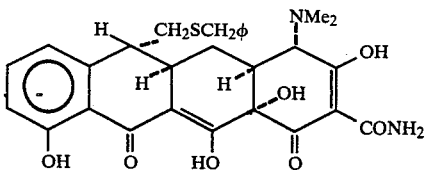

Also useful is the nitrile analog of tetracycline having the structural formula:

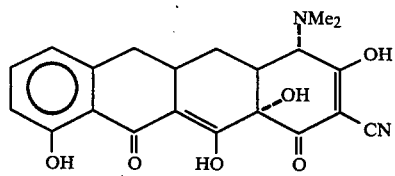

Also useful is the Mono N-alkylated amide of tetracycline having the structural formula:

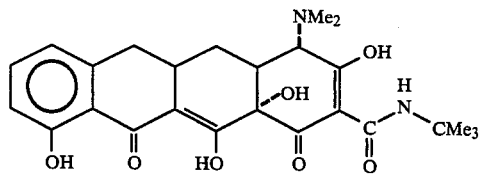

Also useful is the 6 Fluoro demethyltetracycline having the structural formula:

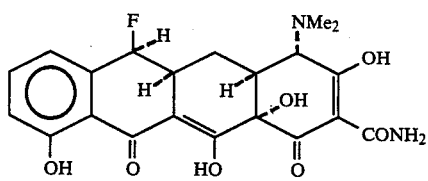

and also 11α-chlorotetracycline having the structural formula:

The special non-antimicrobial or non-antibacterial tetracyclines of this invention are suitably employed per se or in the form of their salts, such as the hydrochloride salts. Other water-soluble salts, such as the sodium or potassium salts, might also be employed.

The tetracyclines of this invention might also be encapsulated for oral administration since, as indicated hereinabove, the tetracyclines of this invention appear to be systemically effective as anti-collagenolytic agents. The tetracyclines of this invention can also be formulated in the form of tablets, capsules, elixirs and the like. The tetracyclines of this invention may be formulated into solutions or suspensions for intramuscular or peritoneal administration. Additionally, the tetracyclines might also be incorporated or formulated into a polymer carrier or delivery system for use topically or locally, such as in the case of the treatment of periodontal diseases, such as for delivery directly into the periodontal pocket.

Suitable polymeric materials useful for incorporating therein the tetracyclines of this invention include ethylene vinyl acetate, polycaprolactone, polyurethane, ethylene cellulose which, after having the tetracyclines incorporated or dispersed therein, are suitable shaped or formed into fibers, sheets, film or particles or granular material capable of being shaped or formed into a suitable form for treatment of periodontal diseases and the like or for direct application to a lesion evidencing pathological collagen destruction or resorption.

As will be apparent to those skilled in the art in the light of the foregoing disclosures many modifications, alternations and substitutions are possible in the practice of this invention without departing from the spirit or scope thereof.

What is claimed is:

1. A method for treating humans or animals suffering from a condition or disease characterized by excessive collagen destruction due to collagen-destructive enzymes which comprises administering to said human or animal an effective anti-collagenase amount of tetracycline having substantially no effective antibiotic or antibacterial activity.

2. A method in accordance with claim 1 wherein said tetracycline is dedimethylaminotetracycline.

3. A method in accordance with claim 1 wherein said excessive collagen destruction is evidenced by ulceration of the cornea.

4. A method in accordance with claim 1 wherein said excessive collagen destruction is evidenced by periodontal disease.

5. A method in accordance with claim 1 wherein said excessive collagen destruction is evidenced by rheumatoid arthritis.

* * * * *